(12) United States Patent
Yarnall et al.

(10) Patent No.: US 8,082,023 B2
(45) Date of Patent: Dec. 20, 2011

(54) TISSUE INTERVENTIONS USING NUCLEAR-EMISSION IMAGE GUIDANCE

(75) Inventors: Stephen T. Yarnall, Poway, CA (US);
David Beylin, Derwood, MD (US);
Larry Hickey, Gainesville, FL (US)

(73) Assignee: Naviscan Inc., Rockville, MD (US)

( * ) Notice: Subject to any disclaimer, the term of this patent is extended or adjusted under 35 U.S.C. 154(b) by 0 days.

(21) Appl. No.: 11/455,241

(22) Filed: Jun. 19, 2006

(65) Prior Publication Data

US 2007/0167749 A1    Jul. 19, 2007

Related U.S. Application Data

(60) Provisional application No. 60/692,243, filed on Jun. 21, 2005.

(51) Int. Cl.
*A61B 6/00* (2006.01)
(52) U.S. Cl. ........................................... 600/436
(58) Field of Classification Search ............ 600/436
See application file for complete search history.

(56) References Cited

U.S. PATENT DOCUMENTS

| | | | |
|---|---|---|---|
| 2,429,438 A | | 10/1947 | Wappler |
| 4,774,948 A | * | 10/1988 | Markham ............... 606/185 |
| 5,158,084 A | * | 10/1992 | Ghiatas ................. 600/434 |
| 5,282,781 A | | 2/1994 | Liprie |
| 5,322,499 A | | 6/1994 | Liprie |
| 5,919,135 A | * | 7/1999 | Lemelson ............... 600/407 |
| 5,954,655 A | * | 9/1999 | Hussman ................ 600/478 |
| 6,093,154 A | * | 7/2000 | Burek et al. ............ 600/564 |
| 6,135,993 A | * | 10/2000 | Hussman ................ 606/2 |
| 6,181,960 B1 | * | 1/2001 | Jensen et al. ............ 600/431 |
| 6,740,882 B2 | * | 5/2004 | Weinberg ............... 250/363.02 |
| 2003/0209096 A1 | * | 11/2003 | Pandey et al. ........... 73/865.9 |
| 2004/0183022 A1 | | 9/2004 | Weinberg |
| 2005/0008869 A1 | * | 1/2005 | Clark et al. ............. 428/421 |
| 2005/0101826 A1 | * | 5/2005 | Bray et al. .............. 600/8 |

FOREIGN PATENT DOCUMENTS

| | | |
|---|---|---|
| WO | WO 88/06864 A1 | 3/1988 |
| WO | WO 98/22022 A1 | 5/1998 |
| WO | 00/41185 A1 | 7/2000 |
| WO | 01/08751 A1 | 2/2001 |

OTHER PUBLICATIONS

Pry, R. et al., "Guide-Wire Reinforcement and Lengthening with coaxial Guide Wires: the crimping technique", Radiology, vol. 174, Jan. 1990, pp. 268-269.

(Continued)

*Primary Examiner* — Brian Casler
*Assistant Examiner* — Saurel J Selkin
(74) *Attorney, Agent, or Firm* — Katten Muchin Rosenman LLP

(57) ABSTRACT

A method and apparatus for marking a lesion in a body part is provided. The method includes the steps of obtaining a first nuclear-emission image of the body part; determining a position of the lesion from the first image; percutaneously introducing a cannula to the determined position; inserting a wire into the cannula, the wire including radioactive material; retracting the cannula while holding the wire in place; and obtaining a second nuclear-emission image of the body part. The second image includes data relating to a position of the lesion and data relating to a position of the wire.

25 Claims, 18 Drawing Sheets

OTHER PUBLICATIONS

Raylman, R.R. et al., "Positron emission mammography—guided breast biopsy" The Journal of Nuclear Medicine, vol. 42, No. 6, Jun. 2001, pp. 960-966.

Khalkhali, I. et al., "Radionuclide-guided stereotactic prebiopsy localization of nonpalpable breast lesions with normal mammograms", Journal of Nuclear Medicine, vol. 38, 1997, pp. 1019-1021.

The International Search Report and the Written Opinion of the International Searching Authority for International Application No. PCT/US2006/023940.

* cited by examiner

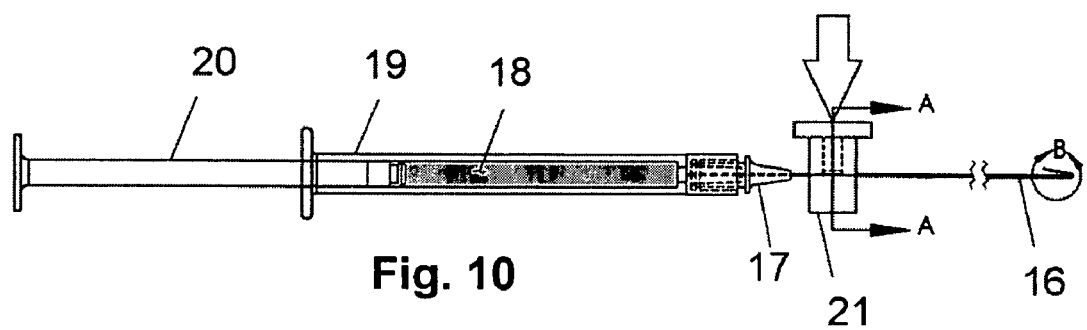
Fig. 10
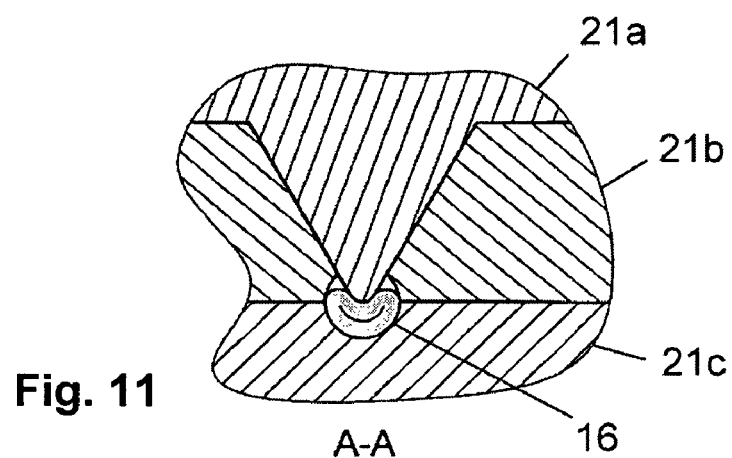
Fig. 11 A-A
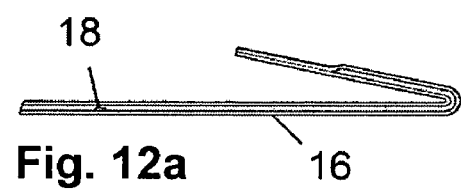
Fig. 12a
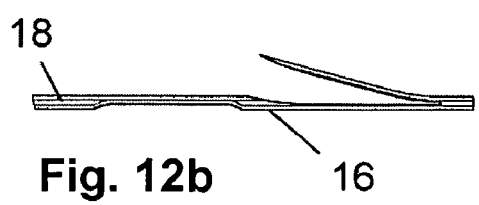
Fig. 12b

TISSUE INTERVENTIONS USING NUCLEAR-EMISSION IMAGE GUIDANCE

CROSS-REFERENCE TO RELATED APPLICATIONS

This application claims the benefit of U.S. Provisional Patent Application No. 60/692,243, entitled "Tissue Interventions Using Nuclear-Emission Image Guidance", filed Jun. 21, 2005, the entire contents of which are expressly incorporated herein by reference.

BACKGROUND OF THE INVENTION

1. Field of the Invention

The present invention relates to an apparatus and a method for detecting and delineating cancerous lesions, and more particularly an apparatus and a method for effective and affordable early detection of cancerous lesions using gamma rays or other radiation to obtain image data. In addition, the present invention relates to applying contrast material to a medical device for the purpose of making it visible to imaging equipment and specifically to applying a radioactive contrast material to a medical device used for tissue marking, sampling, excision or therapy for the purpose of making it visible to nuclear-emission imaging equipment.

2. Description of the Related Art

Cancer is a major threat and concern to the population. Early detection and complete treatment of suspicious or cancerous lesions has been shown to improve long-term survival. Medical imaging modalities such as magnetic resonance imaging (MRI), x-ray, and ultrasound are often deployed to detect small, non-palpable lesions. Once detected, a tissue sample, or biopsy, from the lesion is obtained using position information from one or more of these medical imaging modalities. The tissue sample is then analyzed for the presence of cancer to determine if the lesion requires treatment. If the lesion is found to require treatment (e.g., excision, ablation, or radiation), position information from a medical imaging modality is sometimes used to localize the borders of the lesion so that not more nor less tissue than necessary is treated.

There are a myriad of devices to mark, sample (i.e., biopsy), and treat (e.g., excision, ablation, radiate, or poison) suspicious or cancerous tissue using image localization. Each of these devices produces a signal that can be detected by one or more medical imaging modalities. This signal can be used to ensure the device has been positioned properly in relation to the suspect tissue.

One example of a marking device and method is the common wire-localized biopsy, where an x-ray-opaque guide wire is used to localize non-palpable lesions detected by x-ray or ultrasound for subsequent biopsy or excision. A hollow needle with an open, sharpened tip is inserted percutaneously, into or near the suspect tissue, based on x-ray or ultrasound positioning. The guide wire, typically having a spring-loaded anchoring hook at its tip, is then introduced through the needle and advanced until the anchoring tip projects out the distal end of the needle, at which point the hook is deployed, thus resisting backward displacement of the wire. The needle is then withdrawn, leaving the guide wire in the desired position. The final position of the wire with respect to the lesion is determined and confirmed with subsequent x-ray or ultrasound views. The guide wire is then used in surgery as a physical representation of the position of the lesion to guide a biopsy or excision. It is critical that the position of the guide wire(s) accurately depict the position of the lesion in order to ensure that a proper tissue sample is obtained for analysis, or to ensure that the borders of the lesion are accurately represented for a complete excision of the lesion with minimal complications, scarring and deformity.

Another example of a sampling or biopsy device and method used to localize non-palpable lesions detected by imaging is the common image-guided core-biopsy needle procedure. The core biopsy needle is a minimally-invasive tissue sampling device that can be introduced percutaneously into suspect tissue based on x-ray, ultrasound, or MRI positioning. The needle has an aperture or sampling window for capturing and removing tissue after its position in relation to the lesion has been established by x-ray, ultrasound, or MRI imaging. It is critical that the position of the sampling window is within or directly adjacent to the suspect tissue, in order to ensure that a proper sample is obtained for analysis.

In U.S. Pat. Nos. 6,840,948 and 6,855,140, the contents of both of which are incorporated herein by reference, Albrecht, et al. disclose an example of a method and device to treat cancerous lesions by excision. The disclosures of those two patents describe a means for the intact removal of a lesion under image guidance. A rotatable electrode is inserted into the tissue and positioned adjacent to the lesion, such that by rotationally driving the electrode, it envelops the lesion, thus severing it from the surrounding tissue for intact removal. Imaging is used to assist in placement of the probe, and to assess a desired excision volume. To ensure a complete removal of the cancerous tissue using this method, it is critical to position the electrode directly adjacent to the lesion and confirm the placement with imaging before the excision.

The effectiveness of each of these methods relies on the accuracy of image localization, including x-ray, ultrasound, and potentially MRI, to delineate suspect tissue and to describe the position of the device in relation to that delineation. Thus, the success of the localization and the ensuing procedures relying on that localization are strongly related to the accuracy of the imaging modality.

Nuclear medicine techniques have been adapted for measuring biochemical functions in the human body. One of these methods, known as positron emission tomography (PET), is the detection of gamma rays emitted from tissues after administration of a substance, such as glucose or fatty acids, into which positron emitting isotopes (radiotracers) have been incorporated. A computer algorithm interprets the paths of the gamma rays that result from collisions of positrons and electrons, and the resultant tomogram represents the distribution of the isotope within the imaged tissue.

PET produces images of the body's basic biochemistry or function. Traditional diagnostic techniques, such as x-rays, x-ray computed tomography (CT) scans, or MRI, produce images of the body's anatomy or structure. These techniques can detect diseases when changes in structure or anatomy that occur with disease can be seen.

Biochemical processes are also altered with disease and may occur before there is a detectable change in gross anatomy. PET is an imaging technique that is used to visualize some of these processes that change. PET is a very useful addition to the clinician's diagnostic toolbox, providing significant advances to traditional diagnostic methods.

In cancer imaging, PET that uses the administration of the radiotracer fluorodeoxyglucose (i.e., FDG-PET) is a method of measuring the rate of glucose metabolism within tissue. Increased glucose metabolism is often associated with neoplastic processes. FDG-PET is becoming standard in clinical diagnostic practice, as increased glucose metabolism is one of the earliest methods of cancer detection.

Prior versions of flexible devices for imaging body parts under immobilization and/or compression have employed one detector head above and one detector head below the body part. These configurations allow high spatial resolution to be achieved by minimizing distance between the detector heads and the source of radiation, thereby reducing non-collinearity error, and similarly provide high count sensitivity, due to the fact that radiation detection sensitivity per unit detector area increases as the square of the distance from the source decreases.

Prior versions of flexible devices have featured moving detector heads which conserve component cost and increase access by the user to the body part. Component cost is reduced, since the geometry of acquisition is so sensitive to radiation emitted by the source that it is not necessary to cover the entire face of the body part with detector material. Increased access is achieved by having the detector move out of the way once it has collected enough information to form a high-confidence image. A window is featured that allows a user to mark the body part or perform an interventional or diagnostic procedure once the detector head is out of the way.

Volumetric acquisition of lines of response is obtained with the detector heads, since lines of response impinging one edge of one detector head cross the body part to impinge on the opposite edge of the other detector head. The plurality of such diagonal and/or oblique lines of response passing through a region of tissue provides information as to the depth and strength of sources in the body part under investigation.

As described above, the accuracy of orienting a device in proper relation to the suspect tissue is critical to the success of the ensuing procedure. Thus, in order to perform an effective intervention, such as a biopsy, it is helpful to see both the target (e.g., a suspected tumor) and the interventional device (e.g., a biopsy needle, cannula). Because most interventional devices do not emit radioactivity, they are not visible on PET images. Therefore, it is desirable to find a method of simultaneously imaging the interventional devices and the areas of abnormal tissue with the PET scanner.

U.S. Pat. No. 5,647,374, the contents of which are incorporated herein by reference, describes a stylus comprising a tube having radioactive material in the tip capable of being imaged, the stylus contained within a needle. An image of the tip of the needle can then be traced using gamma ray (also known as nuclear-emission) imaging as the needle penetrates a human body. The position of the radioactive tip of the stylus can be assessed as it approaches a region of suspect tissue, in order to achieve accurate placement within the lesion. Then, the stylus is removed and a guide wire is advanced through the needle. One shortcoming of this method is that once the stylus is removed, it is no longer possible to verify the location, in relation to the suspect tissue, of the guide wire or of any subsequently positioned device. Another shortcoming of this method is that the radioactive stylus device contains only a point source of radioactivity. Thus, the location of the axis of the stylus in relation to the suspect tissue could not be verified with nuclear-emission imaging. This would be a disadvantage in procedures in which more than one visible point is needed. More than one visible point would likely be needed, for example, to demonstrate an orientation of the stylus. Other situations may exist for which a single radioactive point would not be as effective as multiple radioactive points or lines. For example, it would be useful to have more than one radioactive point on the stylus in order to demonstrate the relative extent of a lesion with respect to the radioactive stylus. This would be useful in a lesion bracketing procedure (see, e.g., Silverstein, *Ductal Carcinoma In Situ of the Breast*; 1997, the contents of which are incorporated herein by reference), in which the perimeter of the lesion is demarcated by multiple wires that define all of its perimeter, depth and position. Additionally, if there is only one radioactive point on the stylus, that point might not be visible on the PET image once the radioactive point enters the abnormal region of tissue. Thus, having multiple radioactive points could provide useful redundancy.

SUMMARY OF THE INVENTION

Advantageously, in one aspect, the invention provides a method for using positron emission tomography to obtain positional data relating to a lesion in a body part. The method includes the steps of detecting gamma radiation emitted from the body part; and using the detected gamma radiation to determine the positional data. The method may also include the step of injecting a source of radioactivity into the body part. The step of injecting a source of radioactivity into the body part may include the steps of: charging a hollow tube with the source of radioactivity; introducing the tube into the body part; anchoring the tube proximal to the lesion; and discharging the source of radioactivity. The source of radioactivity may include 2[F-18]fluorodeoxyglucose. The step of using the detected gamma radiation to determine the positional data may include: using at least two detector heads to detect gamma rays; using a coincident timing window to determine lines of response; and using the lines of response to form a representation of a distribution of positron-emitting sources in the body part.

In another aspect, the invention provides a method for using nuclear emission image guidance to obtain positional data relating to a lesion in a body part. The method includes the steps of detecting gamma radiation emitted from the body part; and using the detected gamma radiation to determine the positional data. The method may further include the step of injecting a dose of a radiopharmaceutical into the body part. The step of injecting a dose of a radiopharmaceutical into the body part may include the steps of charging a hollow tube with the radiopharmaceutical; introducing the tube into the body part; anchoring the tube proximal to the lesion; and discharging the radiopharmaceutical. The radiopharmaceutical may be selected from the group consisting of FDG and sestamibi. Alternatively, the radiopharmaceutical may include a source of radioisotope selected from the group consisting of sodium-22, germanium-68, and cobalt-57. The step of using the detected gamma radiation to determine the positional data may include using at least two detector heads to detect gamma rays; using a coincident timing window to determine lines of response; and using the lines of response to form a representation of a distribution of nuclei-emitting sources in the body part.

In yet another aspect, the invention provides a positron emission tomography (PET) scanner system for obtaining image data relating to a compressed and/or immobilized body part. The system comprises a first detector head and a second detector head. Each of the first and second detector heads includes materials that are sensitive to gamma radiation emitted from the body part. Coincidence gating is applied between signals detected by the first and second detector heads. A result of the applied coincidence gating is used to determine the image data. An interventional procedure kit may be used in conjunction with the PET scanner system. The interventional procedure kit may include a first wire that can be filled with radioactive material and then crimped to create a sealed source of radioactivity, and a second hollow wire into which the first wire can be inserted. The first wire may include an anchoring bend or an anchoring barb for anchoring the first wire in a position within the body part. The radioactive material may include 2[F-18]fluorodeoxyglucose, or alternatively, the radioactive material may include a radiopharmaceutical selected from the group consisting of FDG and sestamibi. In another alternative, the radioactive material may include a source of radioisotope selected from the group consisting of sodium-22, germanium-68, and cobalt-57.

In still another aspect of the invention, a method of marking a lesion in a body part is provided. The method includes the steps of obtaining a first nuclear-emission image of the body part; determining an approximate position of the lesion from the first image; percutaneously introducing a cannula to the determined approximate position; inserting a wire into the cannula, the wire including radioactive material; retracting the cannula while holding the wire in place; and obtaining a second nuclear-emission image of the body part. The second image includes data relating to a position of the lesion and data relating to a position of the wire. The radioactive material may include 2[F-18]fluorodeoxyglucose, or alternatively, the radioactive material may include a radiopharmaceutical selected from the group consisting of FDG and sestamibi. In another alternative, the radioactive material may include a source of radioisotope selected from the group consisting of sodium-22, germanium-68, and cobalt-57.

In yet another aspect, the invention provides a method for using nuclear emission image guidance to enable an intervention relating to a lesion in a portion of tissue within a body part. The method includes the steps of: obtaining a first nuclear emission tomograph of the portion of tissue; determining spatial coordinates of the portion of tissue; using the determined spatial coordinates to determine a desired position and orientation for a radioactive marker; obtaining a second nuclear emission tomograph of the portion of tissue, the second tomograph including data relating to the position and orientation of the radioactive marker; and positioning an interventional device using the second tomograph. The method may also include the steps of using the first tomograph to determine whether the radioactive marker is correctly positioned and oriented in the second tomograph; and when it is determined that the radioactive marker is not correctly positioned and oriented, adjusting a position or orientation of the radioactive marker and obtaining an additional nuclear emission tomograph of the portion of tissue that includes data relating to the adjusted position and orientation of the radioactive marker. The method may also include the step of removing the radioactive marker.

The method may also include the step of affixing the radioactive marker to the interventional device. The method may further include the steps of commencing performance of an intervention; and obtaining an additional nuclear emission tomograph during the intervention. The method may further include the steps of commencing performance of an intervention; completing the intervention; and obtaining an additional nuclear emission tomograph after the intervention.

Alternatively, the method may also include the step of placing the radioactive marker within the interventional device. The method may further include the steps of commencing performance of an intervention; and obtaining an additional nuclear emission tomograph during the intervention. The method may further include the steps of commencing performance of an intervention; completing the intervention; and obtaining an additional nuclear emission tomograph after the intervention.

In still another aspect of the invention, a nuclear emission tomography system for obtaining image data relating to a compressed and/or immobilized body part is provided. The system includes a wire that is charged with a radioactive marker; and apparatus for detecting nuclear emission data. When the wire is positioned near a lesion in the body part, the system is configured to provide image data for enabling an interventional device to be positioned and oriented for performance of an intervention relating to the lesion.

BRIEF DESCRIPTION OF THE DRAWINGS

FIG. 10 illustrates a method of sealing the tube by crimping with a tool.

FIG. 11 is an enlarged cross-sectional view of a crimp tool and a crimp-sealed tube.

FIG. 12a is an enlarged section view showing the crimp-seal at the end of the anchoring bend and shows the tube filled with radioisotope.

FIG. 12b is an enlarged section view showing the crimp-seal using a barb for anchoring, according to an alternative embodiment of the invention, and shows the tube filled with radioisotope.

DETAILED DESCRIPTION OF THE INVENTION

Figure 1:
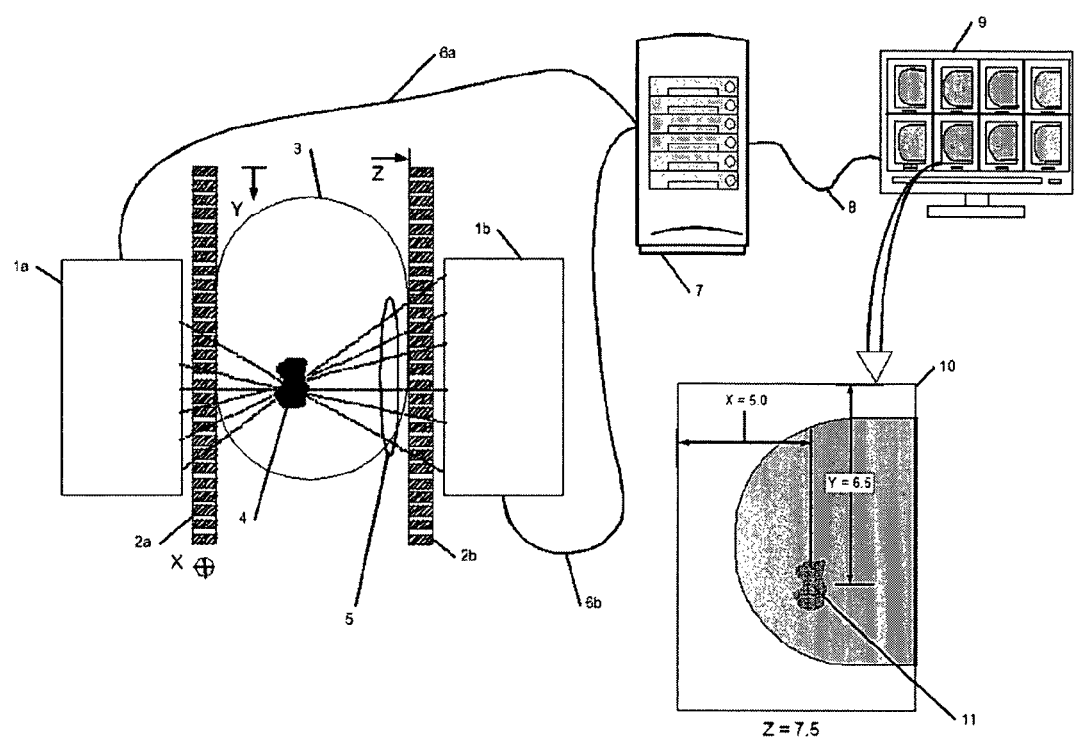
FIG. 1 shows a diagram of a nuclear-emission imaging system for locating and marking the location of a lesion in a breast with a radioactive hook-wire device, according to a preferred embodiment of the invention.

A purpose of the present invention is to provide a method and apparatus to enable nuclear emission guided interventions using an imager that is able to detect emissions from tissue. Preferably, the imager is also capable of providing spatial coordinates or demonstrating spatial positioning of suspect tissue, including tissue that is or is not compressed and/or immobilized.

Accordingly, the present invention provides a method for enabling nuclear-emission-guided interventions. The method includes the steps of: using a nuclear emission tomograph, determining the spatial coordinates of suspect tissue; and then positioning a radioactive marker at a location and orientation relative to the suspect tissue such that an intervention can be performed. A new image is then produced that demonstrates the location and orientation of the radioactive marker with respect to previously and simultaneously identified suspect tissue, which is used to confirm that the position and orientation of the radioactive marker is correct for the ensuing intervention. If the position is not as planned, the radioactive marker can be re-positioned, then re-imaged to confirm the new location. This process can be repeated a number of times until the proper location has been reached. Once the proper location has been reached, the intervention can be performed. This may involve removing the radioactive marker, and positioning an interventional device according to the pre-defined marker location. Alternately, the radioactive marker could be affixed to, or contained within an interventional device, in which case the intervention could take place without removing the radioactive marker. Additional conformational images could be produced to demonstrate the position and location of the radioactive marker affixed to or contained within the interventional device during and after the interventional procedure, which could be used to characterize the action of the intervention (like the removal of radioactive tissue by way of percutaneous lumpectomy or biopsy) or the location of a barbed locational wire with respect to a lesion.

The present invention also provides an apparatus configured to enable nuclear-emission-guided interventions. The apparatus includes: 1) a charged wire (or other device) that could be manually positioned using either a stereotactic method (further described below) or a stepwise method of iteratively positioning the wire/device and imaging the wire/device and its position relative to the suspect tissue. With the stepwise approach, spatial coordinates may not be needed, as direct visualization of the relative placement of the wire/device) to the suspect tissue may be adequate, similarly as is typically done for ultrasound-guided interventions.

Alternatively, the wire/device may be manually positioned using a stereotactic method. This method entails positioning a stereotactic frame adjacent to the suspect tissue. The stereotactic frame provides the ability to locate a trocar, radioactive opturator, or radioactive trocar at a desired position in relation to the suspect tissue. This technique may also be useful for mammographic applications and for magnetic resonance imaging (MRI) applications.

In one aspect of the invention, multiple detector heads are arrayed on two sides of a compressed or immobilized body part which is infiltrated with a positron-emitting radiotracer. Two detector heads may either remain stationary or may be moved in the same direction across a source. The detector heads are attached to lead screws. The z-direction is defined as the direction between the detector heads. Gamma rays from positron annihilation events are emitted by the body part, and converted into electrical impulses within the detector heads, that are collected by a data acquisition system and a computer. When gamma rays are detected in detector heads on different sides of the body part within a coincident timing window, the computer interprets this as a line of response connecting the locations of detection on the detector heads. The lines of response can be used, in conjunction with information about timing of the detected events, to form an image or other representation of the distribution of positron-emitting sources in the body part.

In another aspect, the present invention provides a method for incorporating a vessel or holder for containing a radioactive source into an interventional device for the purpose of providing a radioactive signal from which the position and orientation of the interventional device can be determined using nuclear-emission imaging. A preferred embodiment provides a vessel to be incorporated into or attached to the interventional device whereby a small portion of the total patient dose of radiopharmaceutical in liquid form may be contained.

In a typical nuclear medicine procedure, the patient dose of radiopharmaceutical (e.g., FDG or sestamibi) is delivered to a clinician by a licensed radiopharmacy. The sterile dose is contained in a syringe utilizing a standard male luer fitting to attach a needle for parenteral administration. A very small portion of this patient dose can be allocated to charge an interventional device with a detectable quantity of radioisotope. The concentration of the radioisotope can be ordered or diluted to adjust its volume-specific emission strength such that the signal from the charged interventional device is optimized for simultaneously demonstrating the lesion and the location of the device. Alternatively, the vessel in the interventional device holding the charge can be specified to match up with the standard-delivered dilutions of radioisotope such that one can allocate a minute portion of the radiopharmaceutical dose for charging the interventional device.

One advantage of utilizing a portion of the patient dose is that parameters of the nuclear-emission imaging device are already optimized to image this radioisotope, with its specific emission properties (e.g., energy peak), thus the radioisotope contained by the interventional device can be readily imaged. An alternative approach involves using a long-lived source of radioisotope, such as $Na^{22}$, $Ge^{68}$, or $Co^{57}$, to charge the interventional device, which may have similar, albeit not identical emission properties.

Another advantage of utilizing a portion of the patient dose of radioisotope is maintaining sterility. Many interventional devices are supplied in the sterile condition. Therefore, using a sterile charging method and a sterile isotope provides a procedure-ready device, with no additional steps required to provide sterility.

Another advantage of utilizing a portion of the patient dose of radioisotope for charging an interventional device is safety and convenience in handling sources of radioactivity. Long-lived isotope-sources, such as, for example, $Na^{22}$, $Ge^{68}$, or $Co^{57}$, cannot be readily disposed of in a landfill, and must be stored in compliance with Nuclear Regulatory Commission guidelines. Minute quantities of short-lived sources, such as FDG or sestamibi, that decay at the same rate as the patient dose, need no further facility controls beyond the controls applied to tissue samples, because they contain minute and similar amounts of radiation that is used to characterize suspect tissue. Accordingly, interventional devices charged with short-lived isotopes can usually be disposed of as biological, non-nuclear waste after a short decay time.

Another advantage of utilizing a portion of the patient dose of radioisotope for charging an interventional device is that once the dose is ordered for the patient, it does not cost much more to charge the interventional device with a small portion of the ordered dose. For example, a typical FDG-PET study may use a 5-30 milliCurie patient dose of FDG, while the radioactivity needed for charging the device may be only 1-10 microCurie, which is at most 1/500th of the patient dose, in order to provide an adequate signal without obscuring suspect tissue. In contrast, typical long-lived sealed sources, such as $Na^{22}$, $Ge^{68}$, or $Co^{57}$, can cost hundreds or thousands of dollars and must be replaced when they decay out of the acceptable range for imaging purposes.

Another advantage of utilizing a portion of the patient dose of radioisotope for charging an interventional device is that the liquid-parenteral form of the isotope can be applied to a variety of devices and geometries due to its ability to take on the shape of its containment vessel, and provide a signal that can be used to determine the position and orientation of the device.

Another advantage of utilizing a portion of the patient dose of radioisotope for charging an interventional device is that the manufacturing of the device does not involve the handling or containment of radioactive materials. Many interventional devices can be minimally modified to include a small vessel that can be readily charged in the radioactive containment lab within the health-care facility.

Another advantage of utilizing a portion of the patient dose of radioisotope for charging an interventional or implantable device is that using a short-lived isotope instead of a long-lived isotope eliminates the long-term exposure to the potentially damaging effects of radiation, for example, cancer, that can result from the long-lived isotope.

Alternatively, position sensors or sealed sources containing radioisotope can be incorporated into or attached to an interventional device, either permanently or temporarily, providing a signal or signals that can be used to determine the position and orientation of the device with a nuclear-emission imager.

Figure 14:
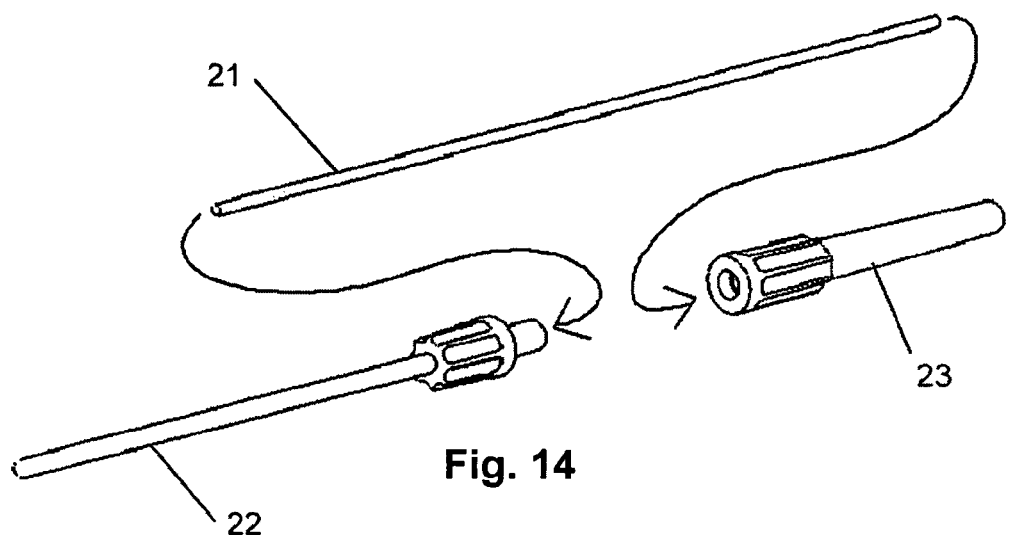
FIG. 14 illustrates an assembly of a radioactive opturator according to a preferred embodiment of the invention.
Figure 15:
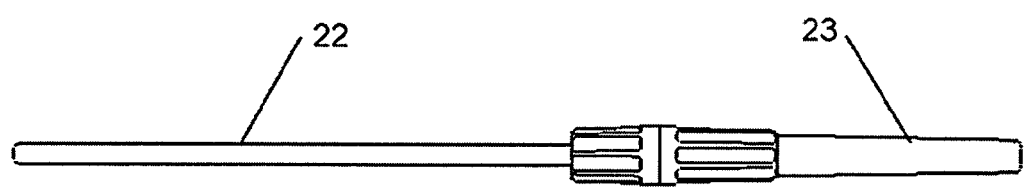
FIG. 15 illustrates a side view of the fully assembled radioactive opturator of FIG. 14.

Referring to FIGS. 14 and 15, in another alternative option for positioning and orienting the interventional device, the radioactive line source 21 may be encapsulated inside a localizing obturator, which includes an obturator main body 22 and a cap 23. This option does not include a hook, but it allows insertion and removal of the line source 21 before and after an intervention. This positioning option works in conjunction with a simple set of components for positioning and orienting the line source 21, guided by software analysis of the lesion position.

In light of the above, it is an object of the present invention to provide one or more of the following:

1. An interventional device for marking suspect tissue that can be imaged using a nuclear-emission based imager and that can be used to guide an intervention.
2. A method to charge an interventional device with one or more radioactive sources such that the device's location and orientation can be determined using nuclear-emission imaging.
3. A safe and simple method to charge and deploy an interventional device with a precise dose of radiation such that it can be readily imaged by a nuclear-emission based imager but such that the device does not obscure the suspect radiolabeled tissue.
4. A method to charge an interventional device with a radiation source that is substantially disposable and is relatively inexpensive.
5. A method to charge an interventional device with a radiation source that is relatively safe and easy to manufacture and/or assemble and/or deploy.
6. A method to charge a sterile interventional device with a dose of radiation while maintaining sterility.
7. A method to charge an interventional device with a convenient dose of radiation that does not require regulatory controls for long-lived calibration sources of radioactivity.
8. A method to charge an interventional device with a short-lived radiation source that can remain permanently implanted without the potential for long-term radiation exposure.
9. A method that can be applied to a variety of device configurations that are design to be utilized in-vivo. Examples of such in-vivo configurations include, for example, cannula, percutaneous tissue extraction device, brachytherapy seed introducer, and biopsy site marker.

The described method and device in the present invention provides advantages in these respects over the prior art. Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

The present invention encompasses methods and devices to localize tissue for interventions using gamma ray (also known as nuclear-emission) imaging. The intent of these methods and devices is to provide a signal or set of signals that can be detected by an external detector to sense position, before and/or during and/or after an interventional procedure, by nuclear-emission imaging. The methods include providing a vessel or holder for a radioisotope that can be incorporated into novel and existing devices. The shape of the radioisotope in the vessel or holder is intended to be readily distinguished from radiolabeled tissue such that it is not confused with, nor does it obscure, biological imaging processes depicted by the radiolabeled tissue, during and/or after deployment of the device.

A preferred embodiment of the present invention comprises an adaptation of the common guide wire for tissue localization that provides an embedded vessel within the wire for a radioactive source. The main elements of the embodiment include a tube, a luer fitting, an anchoring barb, and a vent for filling.

The common guide wire, which is solid, is replaced by a hollow stainless steel tube that is attached, using a coaxial, liquid-tight seal to a female luer fitting, such that a standard male luer syringe can be used to dispense liquid into the hollow interior of the tube.

As is common with tissue localization guide wires, the opposing end of the stainless steel tube is formed into a barb, such that it can provide traction against movement toward the luer end, once it is deployed into a field of soft tissue. The hollow interior of the tube is maintained during the forming process to provide a vent where the air in the tube can escape during the filling process if an air lock is created that would prevent filling the tube.

Charging the tube with a radioactive source requires the steps of connecting the female luer of the tube assembly to a syringe containing a radioactive liquid; dispensing radioactive fluid (e.g., FDG) into the tube until it is filled; crimping the tube at the barb-end and at the luer-end to form liquid-tight seals that permanently contain the liquid; removing the syringe from the tube by separating the luer fittings; capping the female luer to prevent any residual leakage of radioactivity from the luer section; and finally, cleaning the tip of the barb with a sterile swab to clear it of any residual radioactive fluid.

Figure 2:
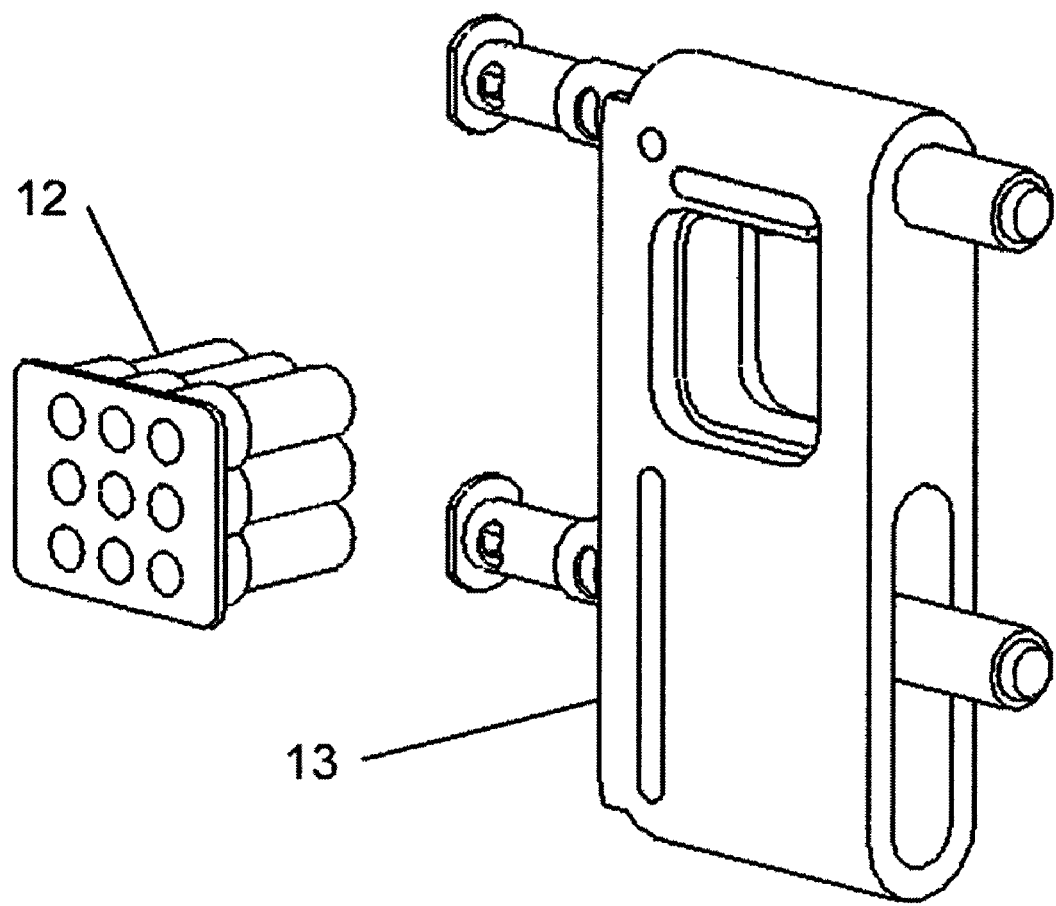
FIG. 2 illustrates a needle guide and holder for use with the system of FIG. 1.
Figure 16:
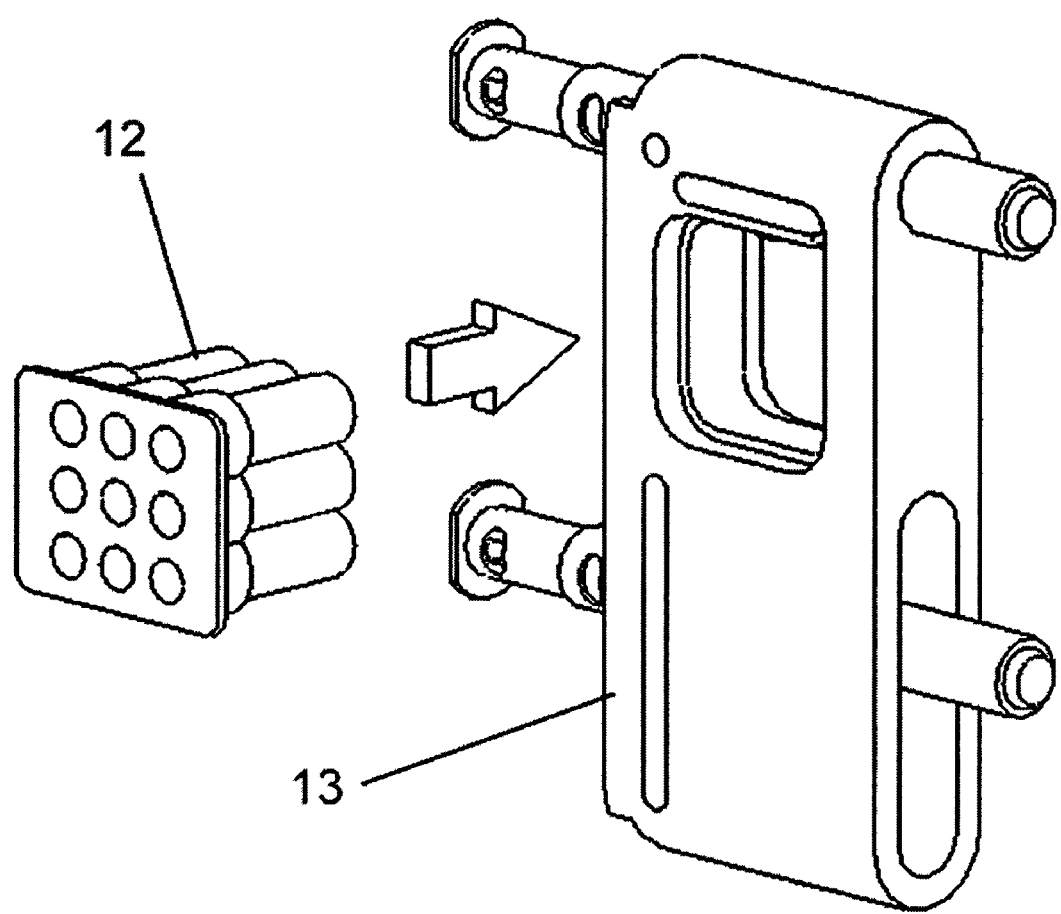
FIG. 16 illustrates an insertion of the needle guide of FIG. 2 into the needle guide holder, according to a preferred embodiment of the invention.
Figure 17:
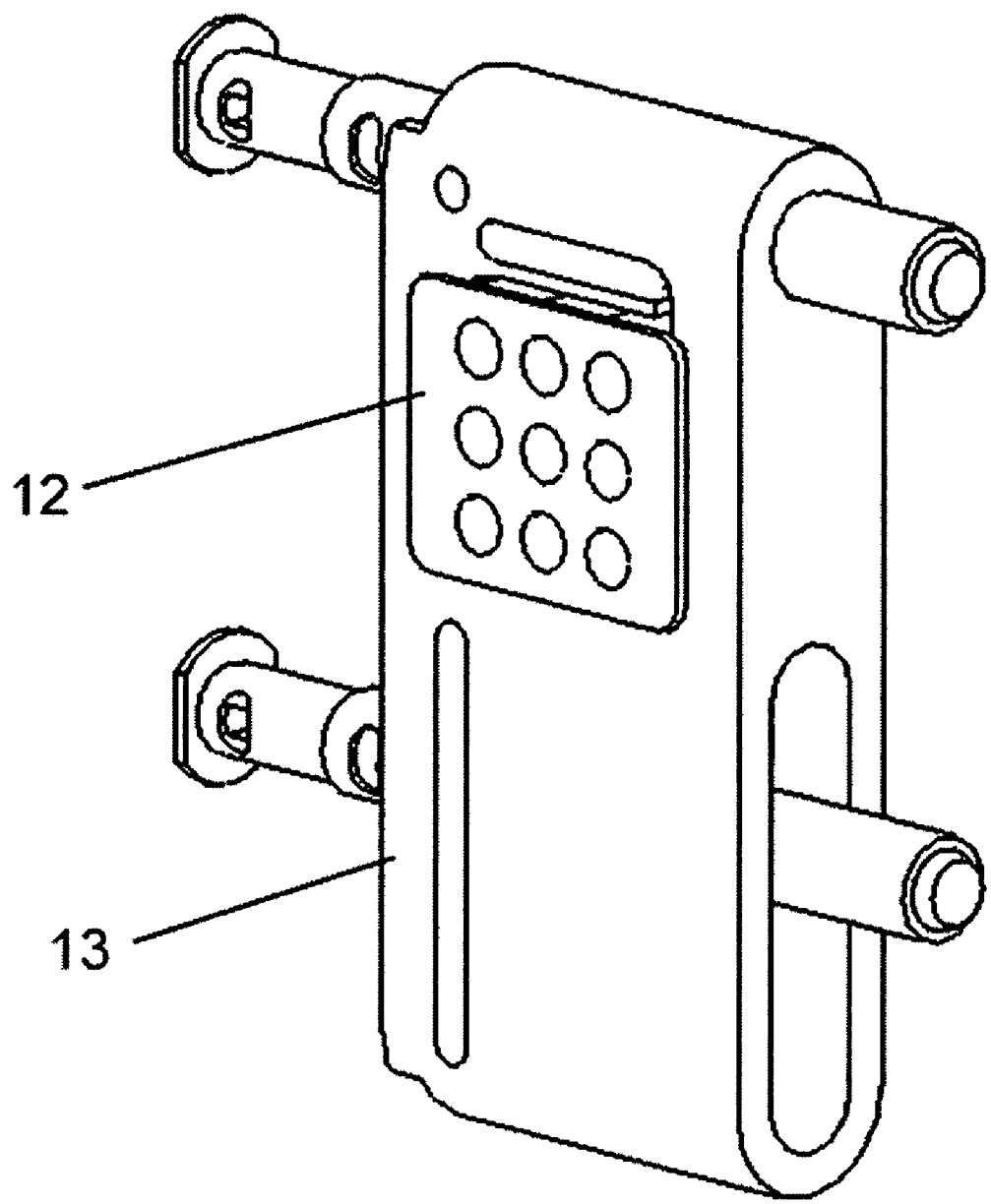
FIG. 17 illustrates the needle guide holder of FIG. 16 with the needle guide fully inserted.

Referring to FIG. 2, a needle guide holder 13 is designed to accept insertion of a standard needle guide 12. The needle guide 12 includes several separate guide holes through which a needle may be inserted. The needle guide holder 13 may be manually positioned with respect to a body part that has a portion of tissue in which it is suspected that a lesion is present. Referring also to FIG. 16, the needle guide 12 is simply inserted into the holder 13, and the full assembly is shown in FIG. 17.

Figure 3:
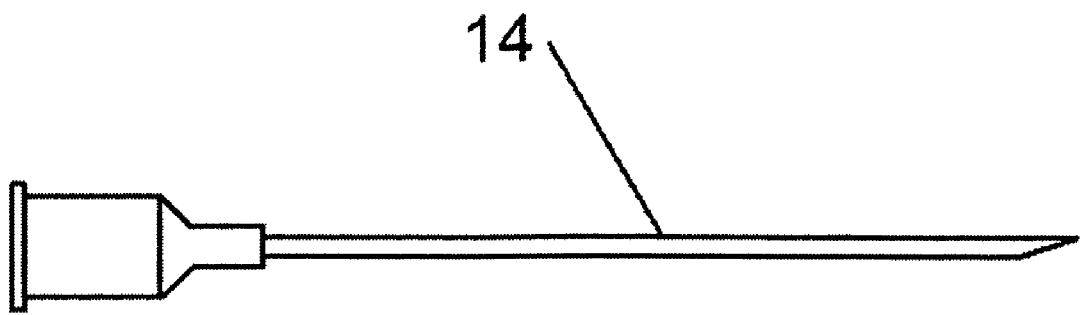
FIG. 3 illustrates a trocar for use with the system of FIG. 1.
Figure 4:
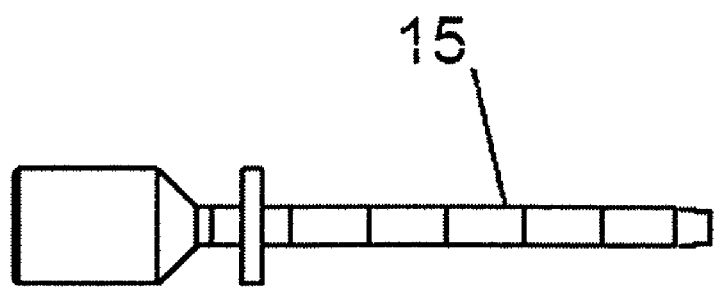
FIG. 4 illustrates a cannula for use with the system of FIG. 1.
Figure 19:
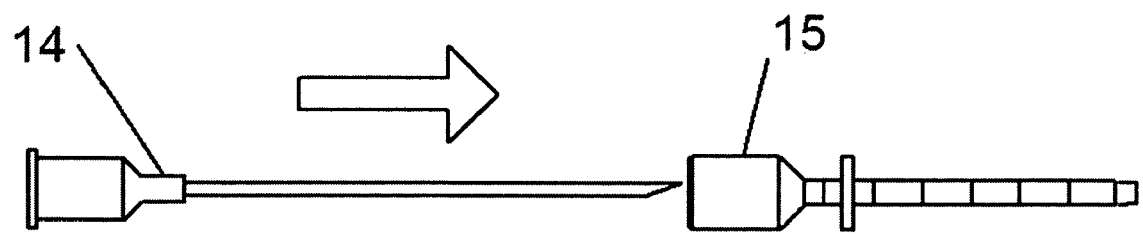
FIG. 19 illustrates the insertion of the trocar into the cannula.
Figure 20:
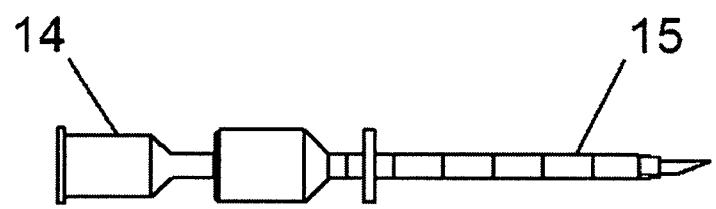
FIG. 20 illustrates a side view of the cannula with the trocar fully inserted.
Figure 21:
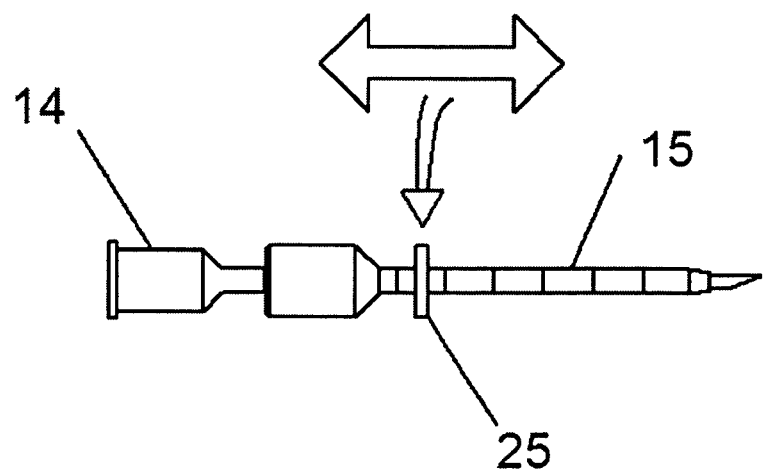
FIG. 21 illustrates how a cannula ring may be adjusted according to the desired depth of the insertion of the cannula into the needle guide holder.
Figure 22:
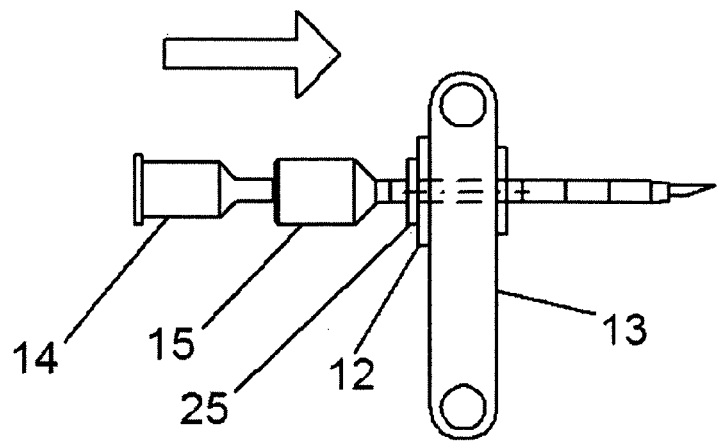
FIG. 22 illustrates the insertion of the trocar and cannula into the needle guide holder to form an access path for the hook wire device.

Referring to FIG. 3, a trocar 14 having a sharpened tip is shown. Referring also to FIG. 4, a cannula 15 provides a tubular path through which the trocar 14 may be safely inserted, as shown in FIG. 19. The fully assembled cannula 15 with inserted trocar 14 is shown in FIG. 20. Referring also to FIG. 21, the cannula 15 also includes a cannula ring 25 that may be adjusted with respect to the shaft of the cannula 15 in order to control a depth at which the cannula may be inserted into the needle guide 12 and holder 13, as illustrated in FIG. 22.

Figure 5:
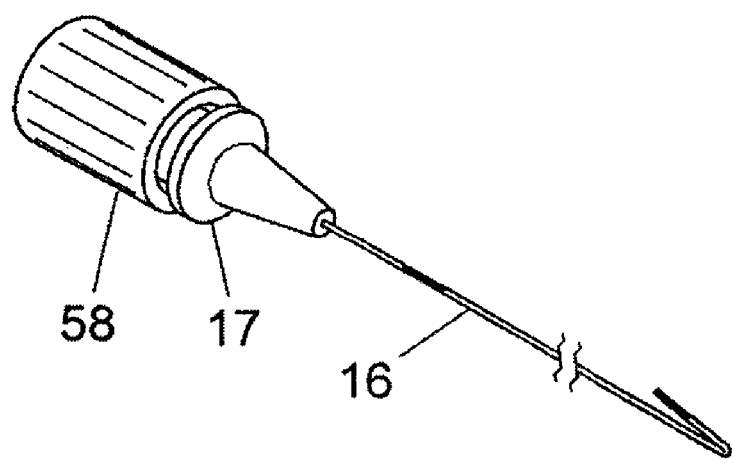
FIG. 5 illustrates an isometric view of a charged and ready-to-use radioactive hook-wire device according to a preferred embodiment of the present invention.

Referring to FIG. 5, an isometric view of a charged and ready-to-use radioactive hook wire device according to a preferred embodiment of the present invention is shown. Each of the components of the device has been sterilized prior to charging, or filling, with radioisotope, and the filling procedure has been conducted in sterile fashion. The hollow wire 16 is filled with a quantity of radioisotope that is optimized for simultaneously demonstrating a lesion and the location of the hook-wire device using a particular nuclear-emission imaging method. Crimp-seals are shown for containing the charge of radioisotope within the wire. The wire is connected to a common female luer fitting 17 that is connected to a syringe for filling the wire prior to crimp sealing. A male luer cap 58 seals the luer fitting on the wire and also facilitates handling the finished device.

Figure 6:
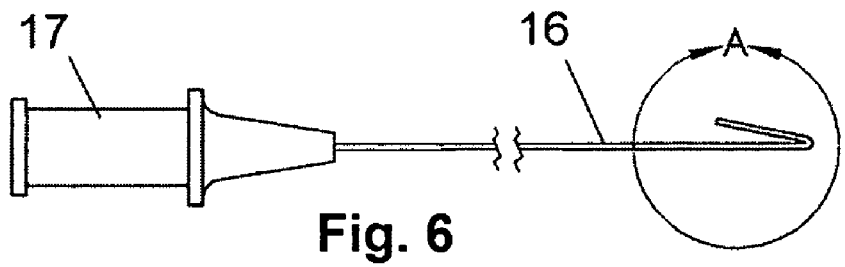
FIG. 6 shows a side view of the hook-wire device shown in FIG. 5 prior to charging with radioisotope.

Referring to FIG. 6, a side view of the hook wire device of FIG. 5 is shown, prior to charging (i.e., filling) with radioisotope. In a preferred embodiment, the device employs a stainless steel tube 16 of a size, for example, 30 G, that can be readily implanted through a cannula, such as a 20 G needle, in a minimally-invasive radiological procedure.

Figure 7:
FIG. 7 is an enlarged section view of a bend used to anchor the end of the hook wire device proximal to the lesion.
Figure 8:
FIG. 8 is an enlarged section view showing a barb used to anchor the end of the hook wire device proximal to the lesion, according to an alternative embodiment of the invention.

Referring to FIG. 7, an embodiment of the end of the wire 16 is shown. The wire 16 includes a bend for anchoring proximal to the lesion. The wire 16 includes a formed tube for filling. As is common with guide wires, the bend provides traction against pulling on the wire during subsequent interventional procedures. Referring to FIG. 8, an alternative embodiment of the end of the wire 16 is shown. In this embodiment, instead of a bend, the wire 16 includes a barb for anchoring proximal to the lesion. The advantage of this alternative embodiment is that it can be introduced through a smaller diameter cannula, for example, a 23 G needle, for improved patient comfort. This is particularly useful in cases where multiple wires are used to describe the boundaries of a lesion, and the patient must be asked to tolerate multiple insertions of the cannula.

Figure 9:
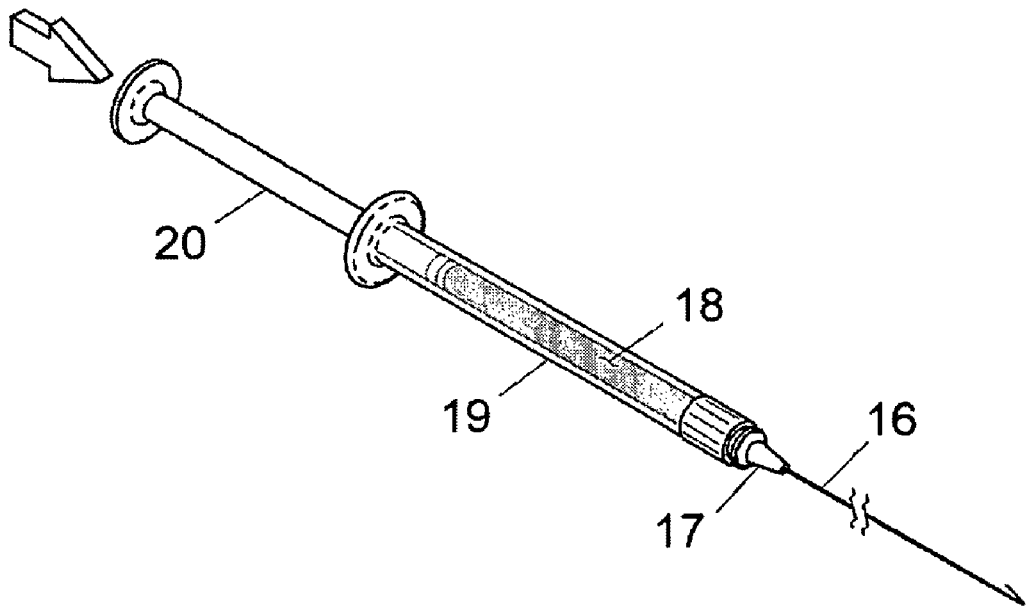
FIG. 9 illustrates a method of filling the tube using a syringe filled with radioisotope.

Referring to FIG. 9, a method of filling the tube using a syringe filled with radioisotope according to a preferred embodiment of the present invention is illustrated. The female luer 17 at the distal end of the wire 16 is connected to the standard male luer on syringe body 19 containing radioisotope 18. The plunger 20 is depressed to transfer radioisotope from the syringe to the hollow wire 16. The end of the wire 16 is vented, for example, as shown in either FIG. 7 or FIG. 8, to allow filling.

Figure 26:
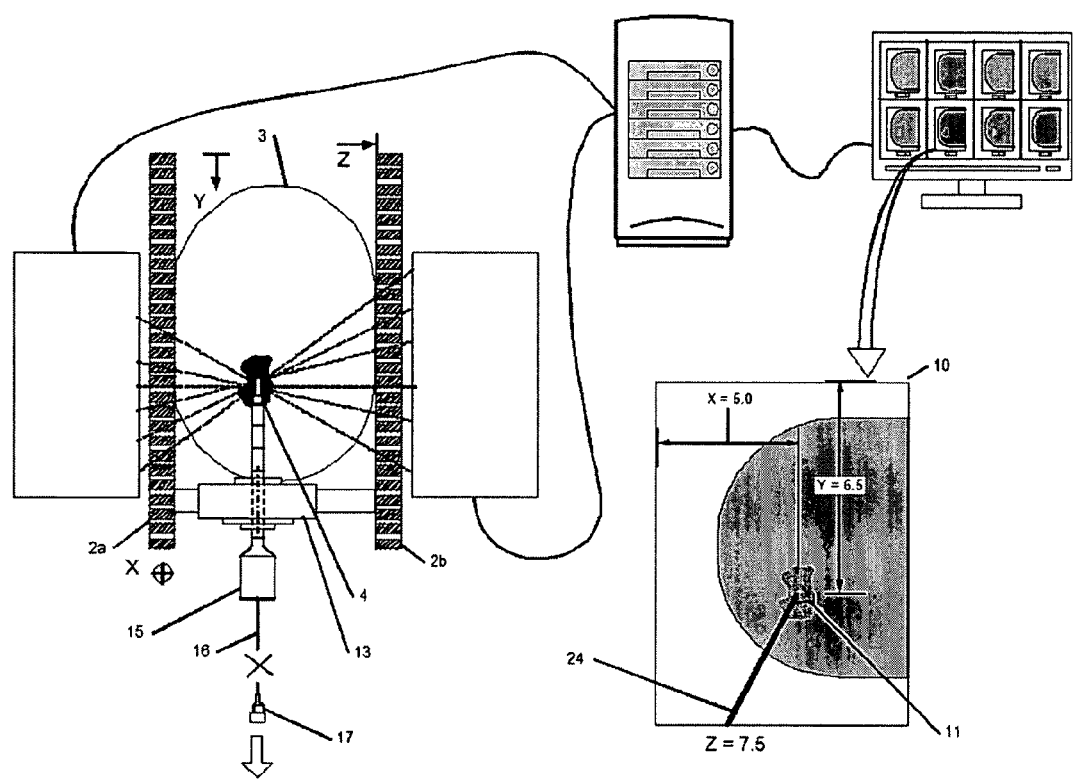
FIG. 26 shows the luer fitting being removed from the radioactive hook-wire device to allow the cannula to be removed from the breast.

Referring to FIG. 10, after filling the hollow wire 16 with radioisotope 18, the ends must be sealed to prevent loss of the fluid radioisotope. This is preferably done prior to removing the wire 16 from the syringe 19. Sealing is done with crimp tool 21 at both proximal and distal ends of the wire 16. The crimp tool 21 is preferably supplied as a sterile disposable component. Referring also to FIG. 11, a cross-sectional view through the crimp tool 21 and the crimp-sealed tube 16 is shown. The crimp tool 21 includes a moveable plunger 21a, held in place by body 21b, and pressing against base 21c, to form the crimp. The length of the crimp along the wire at the distal end is sufficient (e.g., 4 mm) for positioning scissors to clip off the luer fitting during the localization procedure, as illustrated in FIG. 26.

Referring to FIG. 12a, an enlarged section view of a crimped wire 16 having an anchoring bend, similar as the wire in FIG. 7, is shown. In FIG. 12a, the crimp-seal is illustrated as an indentation at the end of the anchoring bend, and the tube is filled with radioisotope 18. Referring to FIG. 12b, an enlarged section view of a crimped wire 16 having an anchoring barb, similar as the wire in FIG. 8, is shown. In FIG. 12b, the crimp-seal is illustrated as a slight indentation in the wire 16, and the tube is filled with radioisotope 18.

Figure 13:
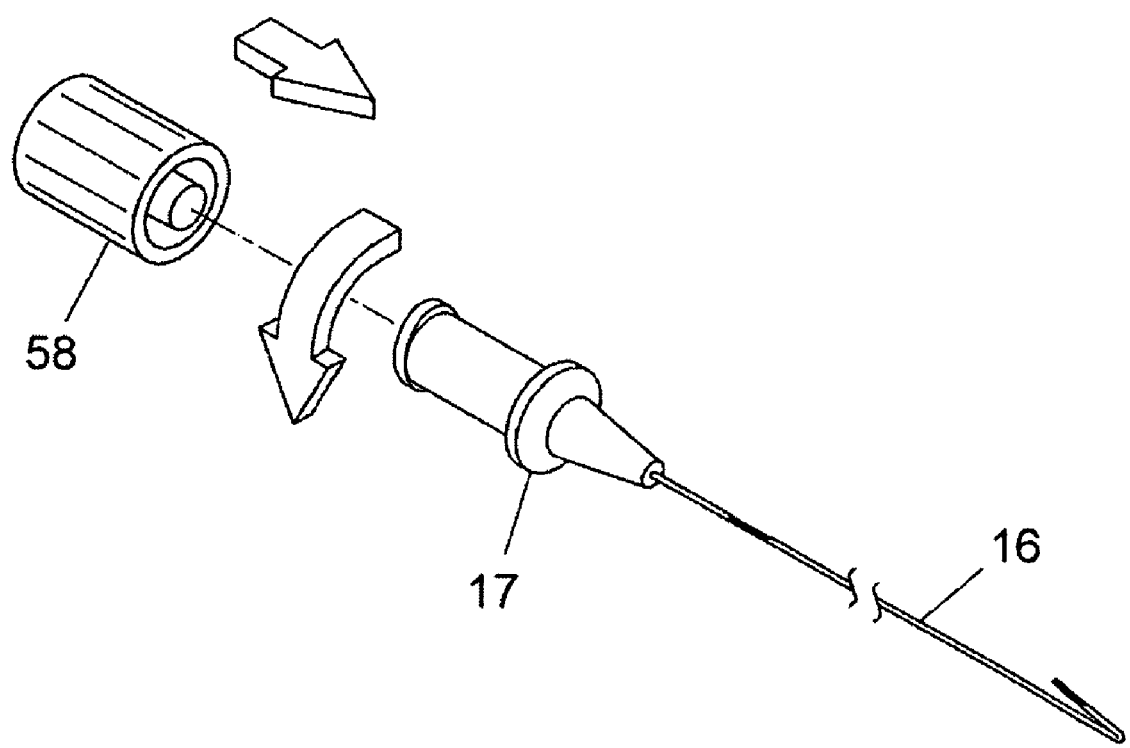
FIG. 13 illustrates the distal end of the charged and crimp-sealed wire being capped with a luer cap.

Referring to FIG. 13, a small amount of radioisotope 18 will be present prior to filling the wire 16 at the distal and proximal ends of the wire. To prevent any leakage of radioisotope past the distal end of the luer fitting 17, a luer cap 58 is attached after the crimping procedure. The luer cap 58 also facilitates handling and deploying the thin wire 16. Any residual liquid radioisotope at the proximal end of wire 16 can be wiped off with a sterile swab.

A lesion marking method using the radioactive hook-wire device as described above will now be described. The fundamental requirements for a lesion marking method according to a preferred embodiment of the present invention include: a nuclear-emission imaging system that can display tomographic images; stabilization of the suspect tissue in relation to the imaging system; and a cannula for introducing the radioactive hook-wire device and the hook wire device.

Marking a lesion with the radioactive hook-wire device requires the steps of: 1) obtaining a nuclear-emission image of the stabilized suspect tissue to determine the position of lesion in three dimensions; 2) percutaneously introducing a hollow cannula with a sharpened tip, for example, a 20 G needle, to the desired position in relation to the lesion; 3) introducing the radioactive hook-wire device into the cannula until the tip if the wire contacts the tissue at the distal end of the cannula; 4) retracting the cannula while holding the radioactive hook-wire device in place; and 5) re-imaging the wire to demonstrate its position in relation to the lesion. Note that prior to fully retracting the cannula, the luer fitting must be removed, for example, with scissors, from the hook-wire device. Alternatively, the radioactive hook-wire device can be pre-loaded into the cannula prior to or during its percutaneous advance toward the lesion. Pre-loading the cannula provides the ability to obtain serial nuclear-emission images for tracking the advance of the cannula such that it can be steered directly to the desired position in the case of deep lesions.

Referring to FIG. 1, a diagram of a nuclear-emission imaging system for locating and marking the location of a lesion in a breast with the radioactive hook-wire device is shown. Fenestrated plates 2a, 2b stabilize the breast 3, which contains a lesion 4. A positron-emitting radiotracer, such as FDG, has preferentially concentrated in lesion 4, emitting coincident gamma rays 5 that are absorbed by the detectors 1a, 1b. Signals from detectors 1a, 1b are sent via cables 6a, 6b to a processor unit 7 that subsequently determines the three-dimensional distribution of radiotracer. A graphical representation of the distribution is then sent via a cable 8 to display 9, where the location of the radiotracer concentrating in the lesion 4 can be determined in relation to the fenestrated paddles 2a, 2b. In this example, a selected display 10 of the tomographic slice representing a Z-depth of 7.5 most clearly demonstrates the lesion, shown as 11, at X-dimension 5.0 and Y-dimension 6.5. Thus, the coordinates of the lesion in relation to the fenestrated plates 2a, 2b are: X=5.0, Y=6.5, Z=7.5.

Figure 18:
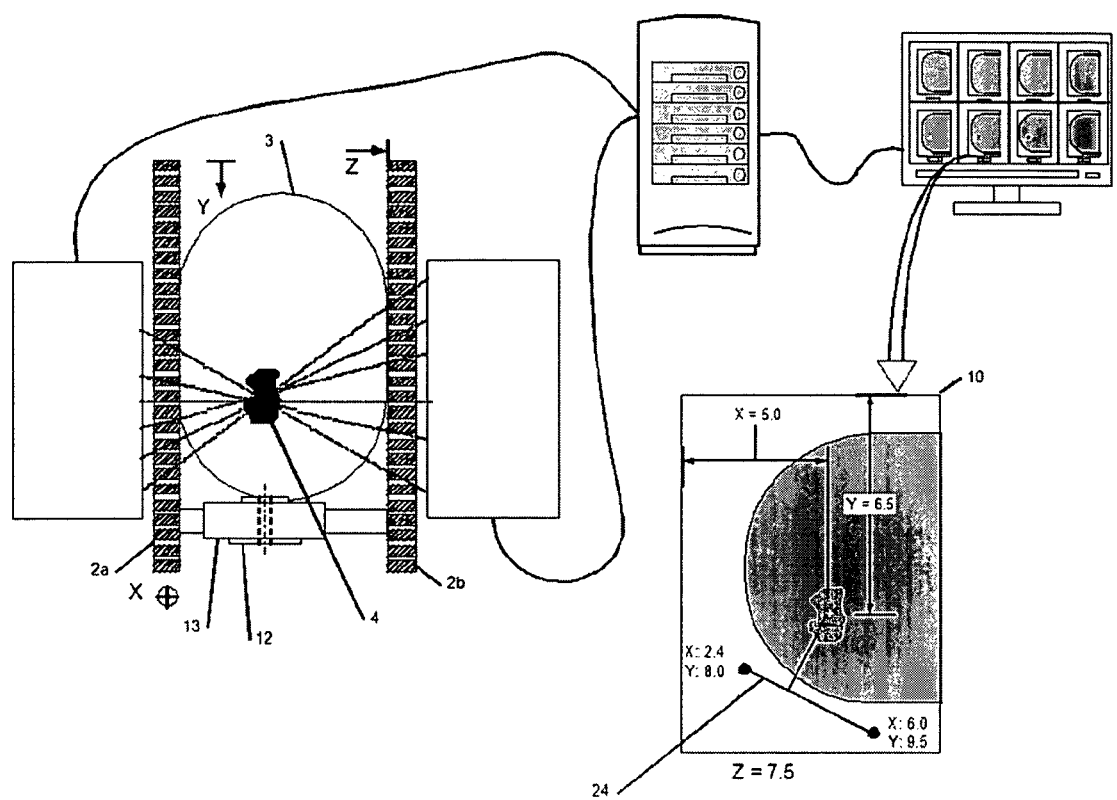
FIG. 18 shows a display that shows coordinates determined by the nuclear-emission imaging system for introducing the needle guide holder into the site of a lesion according to a preferred embodiment of the invention.

Referring to FIG. 18, the assembly of the needle guide 12 and the needle guide holder 13 is positioned advantageously with respect to the breast 3 and the lesion 4. An image on selected display 10 shows the coordinates for the needle guide assembly: One end of the needle guide holder 13 is located at X=2.4, Y=8.0, Z=7.5; and the other end of the holder 13 is located at X=6.0, Y=9.5, Z=7.5.

Figure 23:
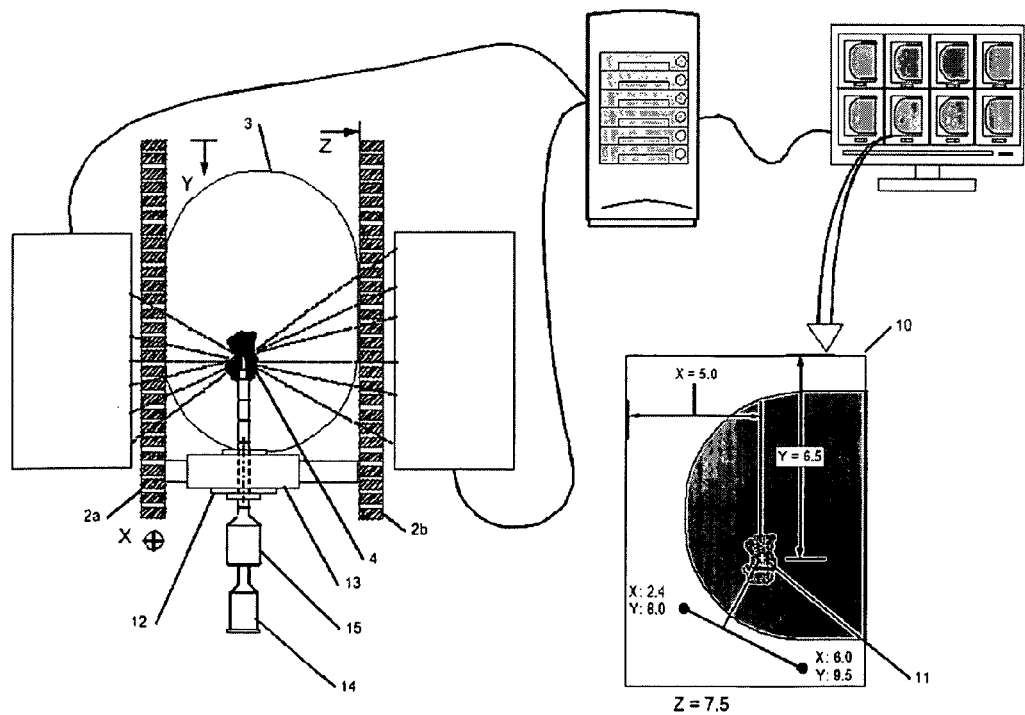
FIG. 23 illustrates the system of FIG. 1 with the trocar and cannula inserted into the site of a lesion.
Figure 24:
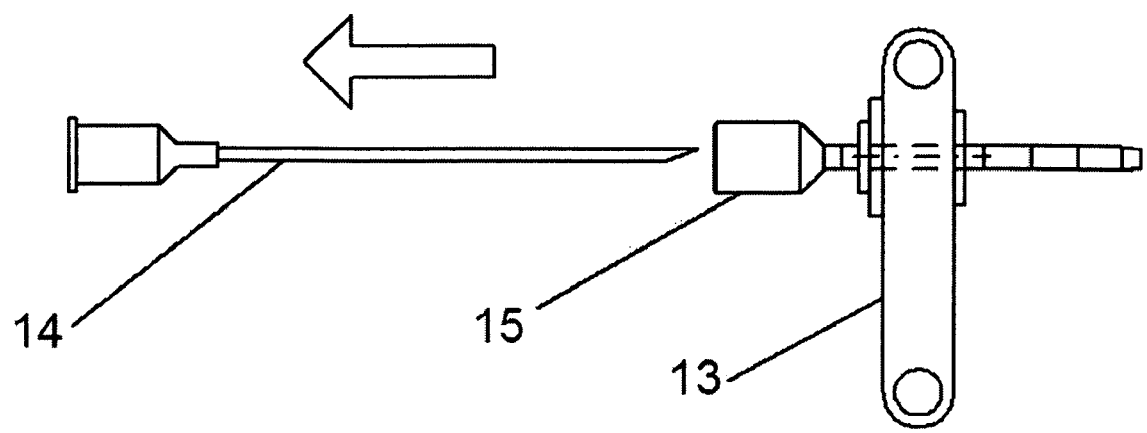
FIG. 24 illustrates the removal of the trocar from the cannula.
Figure 25:
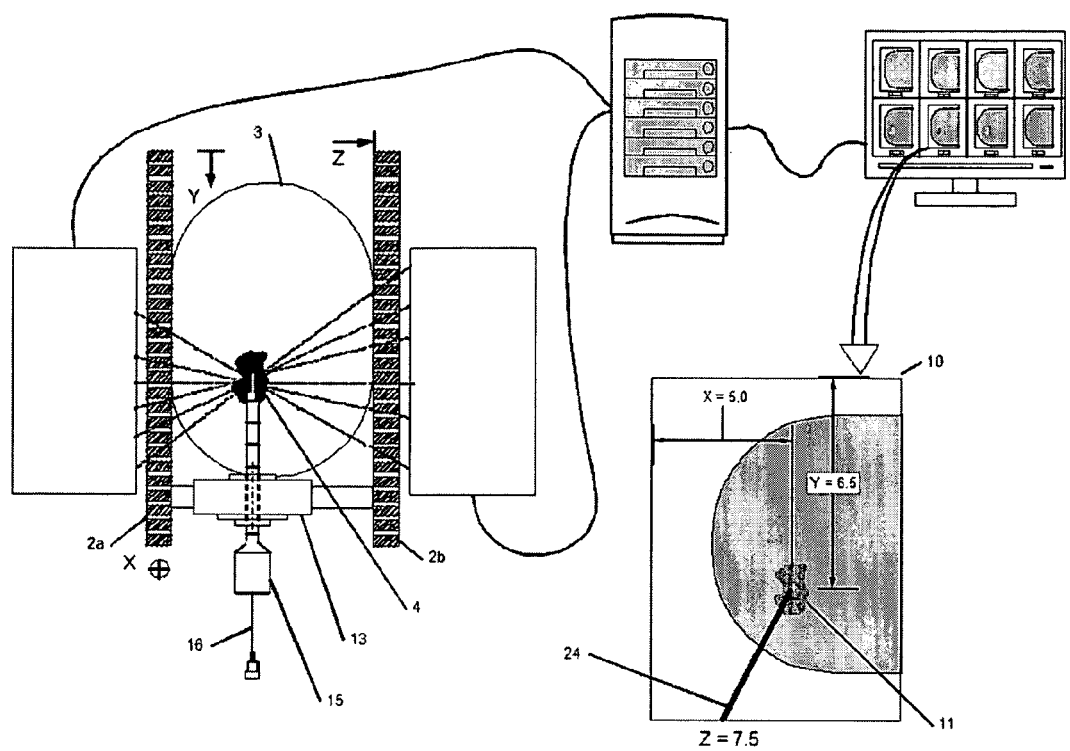
FIG. 25 shows the radioactive hook wire device introduced to the site of a lesion through the cannula.

Referring to FIG. 23, with the needle guide assembly positioned as described above, the assembly of the cannula 15 and the trocar 14 with a sharpened tip is percutaneously introduced into the site of the lesion 4 via the needle guide 12 at the coordinates determined in the system of FIG. 1. Referring to FIG. 24, having created the access path to the lesion 4 with the sharpened tip, the trocar 14 may be removed from the cannula 15. Referring to FIG. 25, the radioactive hook wire 16 is introduced to the site of the lesion 4 through cannula 15. Note that gamma rays 5 now include those being emitted from the radiotracer in the lesion 4 and gamma rays from the radioactive hook-wire 16. The nuclear-emission imager detects the gamma rays from the radioactive hook-wire 16, which are represented on the display 10 at 24, in addition to the gamma rays from the lesion 4 which are now represented on the display as 11.

Referring to FIG. 26, the luer fitting 2 is removed from the radioactive hook-wire 1, preferably by clipping it off at the center of the distal crimp, to maintain the seal at either end. The cannula 15 is then removed from the breast 3 by sliding it over the radioactive hook-wire 16 while maintaining forward pressure on the hook-wire 16 until its anchoring bend or barb is deployed.

Figure 27:
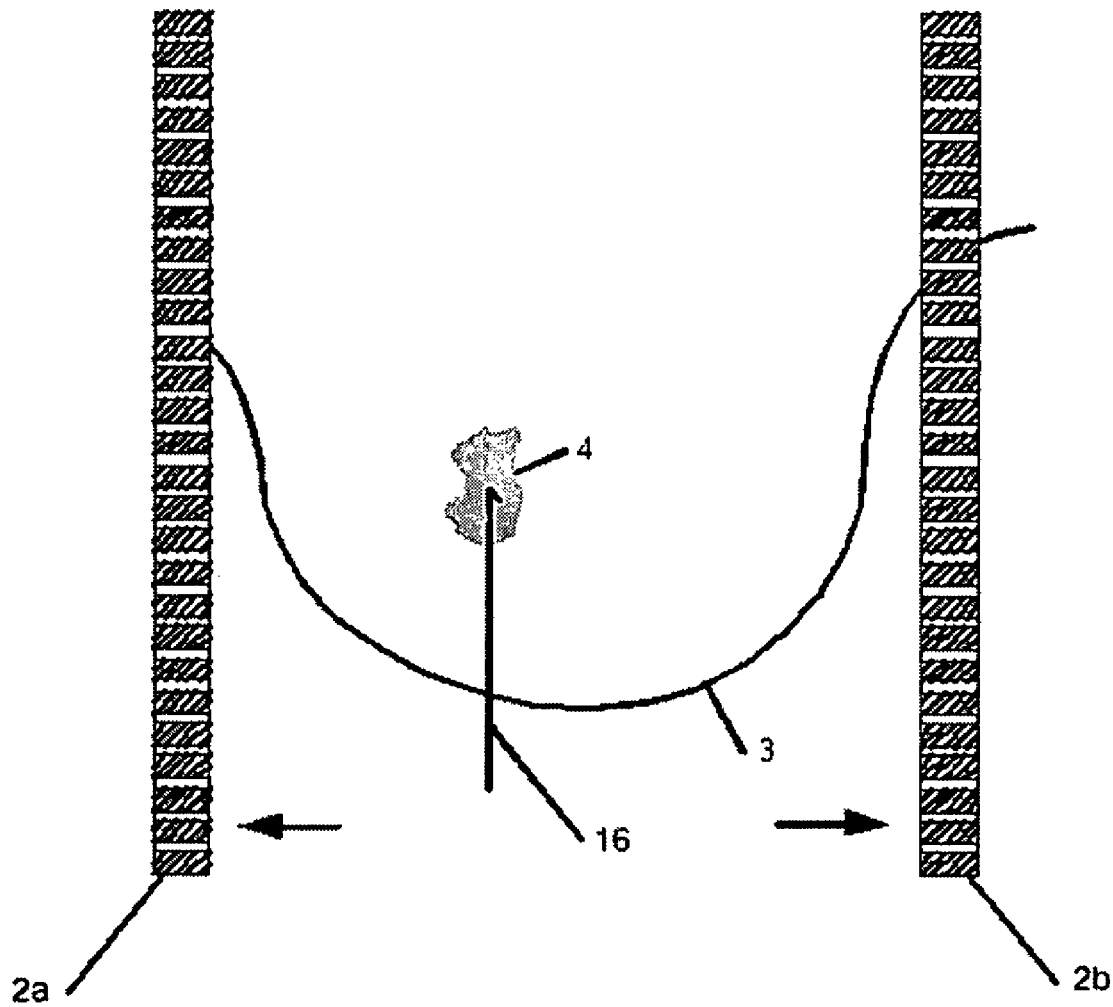
FIG. 27 shows the breast released from the system with the radioactive hook-wire device positioned to be externally accessible for guiding interventions.

Referring now to FIG. 26, the radioactive hook-wire device 16 is held in place with its anchoring bend or barb proximal to the lesion, and the final nuclear emission image 24 of the hook-wire 16 is displayed to confirm its final position in relation to the lesion 11, 4. Referring to FIG. 27, the breast 3 is released from the fenestrated plates 2a, 2b. The radioactive hook-wire device 16 is now accessible for guiding interventions relating to lesion 4.

Figure 28:
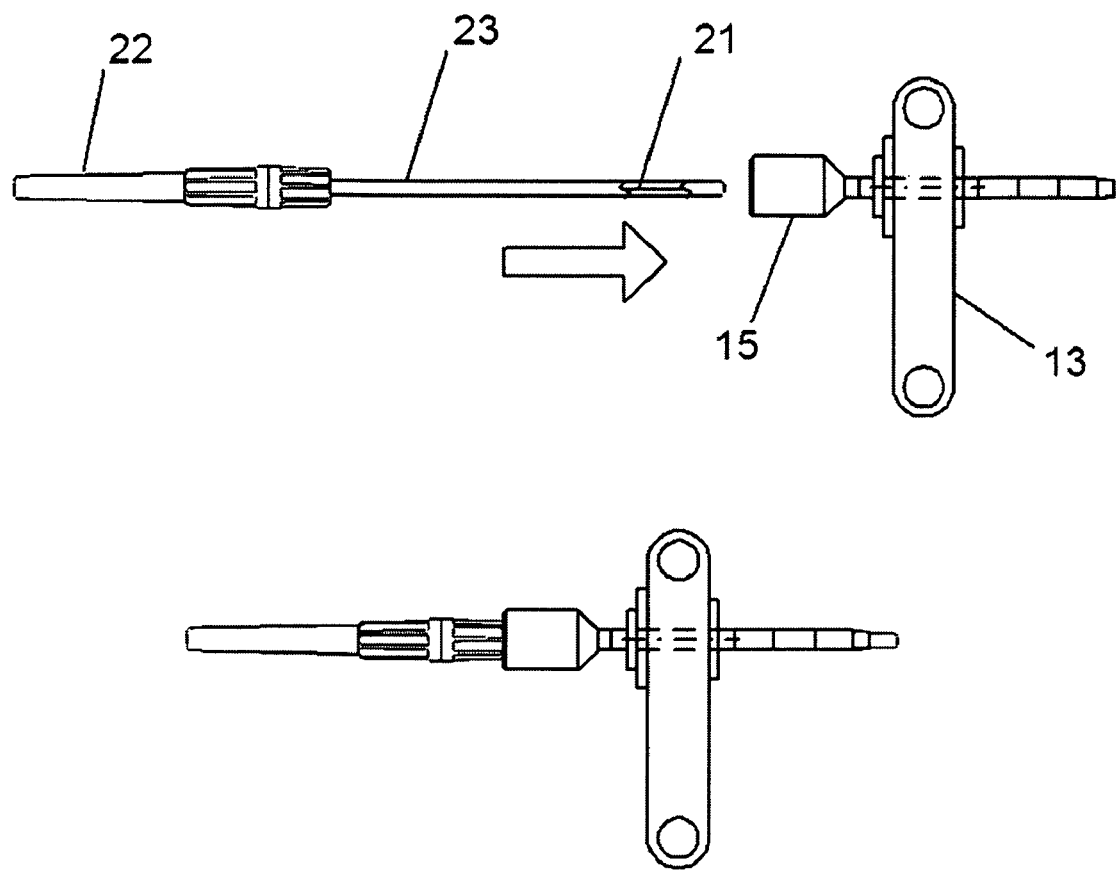
FIG. 28 illustrates the insertion of a radioactive line source into the body part proximal to the lesion via the access path.
Figure 29:
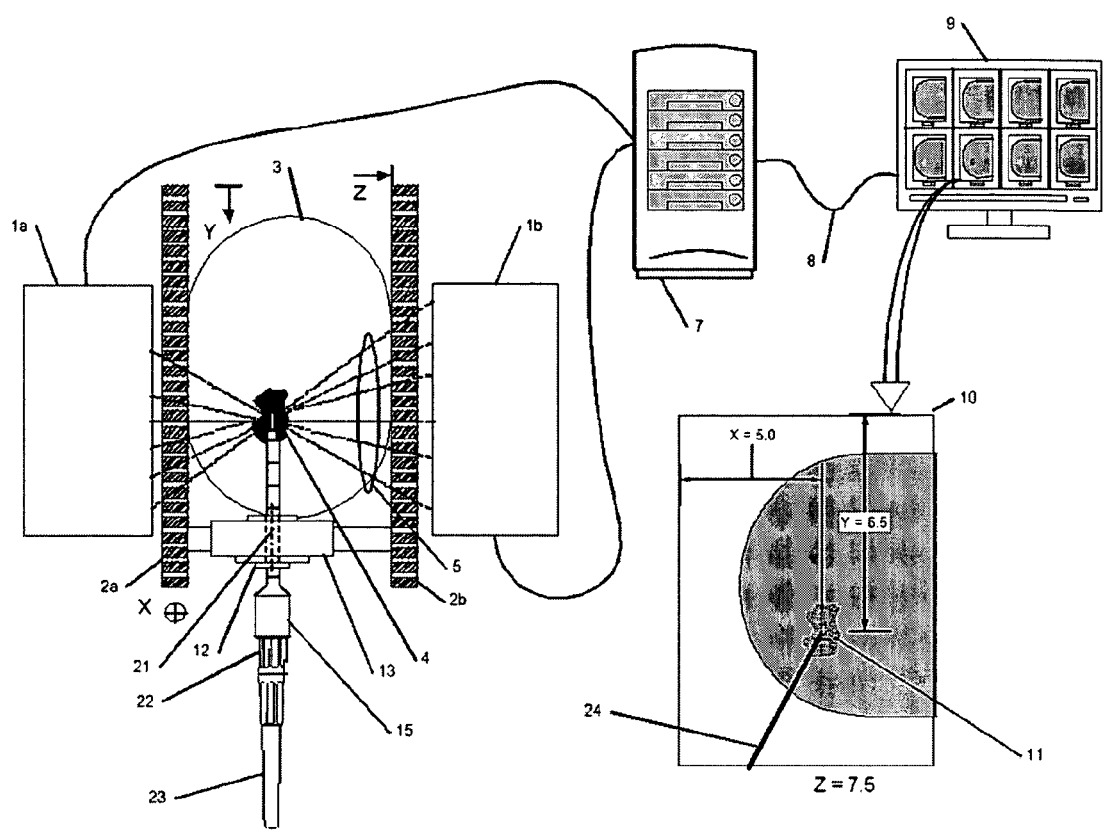
FIG. 29 shows the alternative radioactive device (i.e., line source with no hook) held in place with its end proximal to the lesion.

A simple lesion marking method using a removable radioactive line source and a biopsy method, both using the same localization set-up between stabilization plates, will now be described. Referring to FIG. 29, plates 2a, 2b stabilize the body part 3 (e.g., a breast), which contains a lesion 4. Detectors 1a, 1b are behind the plates 2a, 2b. The placement of the detectors behind the plates has the effect of opening up access for marking and biopsy between the plates, as opposed to requiring access through the plates. Similarly as described above in the previous example, a positron-emitting radiotracer concentrated in lesion 4 emits gamma rays 5 that are absorbed by the detectors 1a, 1b and translated via software into a graphical display showing the lesion's position relative to the plates 1a, 1b on three axes. The software displays optional directions of access between the plates 1a, 1b. The clinician can then select a direction of access. The software then displays two x-y coordinates for positioning the needle guide holder 13. In the configuration shown, the clinician locks the needle guide holder 13 into place between the plates 1a, 1b, using spring-loaded pins that lock into each plate. The z-axis location is adjustable by sliding the needle guide holder 13 up and down on these spring-loaded pins. A standard needle guide 12 is inserted into the needle guide holder 13. In the configuration shown, this action locks the needle guide holder in the z-axis. An introducer stylet (e.g., a trocar) is inserted into an introducer sheath. Referring also to FIG. 21, the cannula 15 is adjusted for the proper depth via the cannula ring 25. The trocar 14 and cannula 15 are inserted through the proper hole in the needle guide holder and into the breast. The trocar 14 is then removed. Referring also to FIG. 14, a line source 21 has been injected into, and sealed within, a thin tube in a manner similar to the aforementioned hook-wire (but without the hook). Referring also to FIG. 15, the sealed line source 21 is then encapsulated inside a sterile or sterilizable cover that includes a main body portion 22 and a cap 23. Referring also to FIG. 28, the encapsulated line source 21 is introduced to the site of the lesion through the cannula 15 and the needle guide 12. The display 10 confirms with a new scan that the line source 21 is positioned properly, as shown on display 10 at 24, relative to the lesion 4, shown on display 10 at 11. The localizing opturator is removed and replaced with the biopsy needle through the same needle guide. After biopsy is performed, a standard non-radioactive hook-wire may be inserted through the cannula 15 for guiding interventions beyond biopsy. The cannula is then removed, and the breast is released from the plates.

The apparatus includes the following components: a) holder 13; b) needle guide 12; c) paddles 2a, 2b; d) radioactive localizing opturator (i.e., a sealed radioactive line source) 21; e) trocar 14; f) cannula 15; and g) imager 10. For the radioactive localizing opturator 21, either of two types of lines source may be used: 1) a line source inside sterile plastic cover, or 2) a reusable and sterilizable line source.

A method of using the apparatus shown in FIGS. 1 and 29 according to a preferred embodiment of the present invention includes the following steps: 1) obtain an image of the lesion; 2) localize the lesion; 3) position the holder (i.e., determine the x and y coordinates of "bombsites" on paddles and the z coordinate between paddles); 4) insert the needle guide (locking holders in z position); 5) insert the trocar into cannula; 6) adjust the cannula ring to an appropriate depth; 7) insert the trocar and the cannula to form an access path; 8) remove the trocar from the cannula; 9) select the required strength (i.e., radioactivity level) for the line source; 10) insert the radioactive opturator into the access path formed by the trocar; and 11) confirm localization by scanning for a new image.

Alternatively, embodiments of the present invention may be utilized at a variety of anatomical sites, such as, for example, tissue removal sites, biopsy sites, polyp sites, lesion sites, or other sites of interest. An organ such as the lung, the prostate gland, or the liver may qualify as such an anatomical site. The marker may be permanently implantable such that the marker will remain permanently at the tissue site unless intentionally removed.

While the foregoing detailed description has described only certain embodiments of this invention, it is to be understood that the above description is illustrative only and not limiting of the disclosed invention. For example, the method of the present invention may also be carried out by charging a lumen with a sterile and sealed line-source of radioactivity for placement within the cannula of a tissue-extraction device, then utilizing the signal from the line source to indicate the position and orientation of the cannula in relation to the suspect tissue by nuclear-emission imaging. While preferred embodiments of the present invention have been shown and described herein, it will be obvious to those skilled in the art that such embodiments are provided by way of example only. For example, the lumen in the previous example containing the sealed line source could be used to position a cannula of a brachytherapy seed-loader within a lesion using nuclear-emission imaging to determine the position of the cannula in relation to the lesion. Numerous variations, changes, and substitutions will now occur to those skilled in the art without departing from the invention. For example, the vessel containing the radioactive source could be designed to harbor a solid source of radioisotope, enveloping it completely or partially, provided the orientation and location source could be used to determine the location of a device holding the source using nuclear-emission imaging.

What is claimed is:

1. A method for using positron emission tomography to obtain positional data relating to a lesion in a body part into which a radiopharmaceutical substance has been injected, the method comprising the steps of:
    detecting gamma radiation emitted from the lesion in the body part using a positron emission tomography device;
    using the detected gamma radiation to determine the positional data;
    inserting a fixed-geometry radioactive marker into the body part, wherein gamma radiation emitted from the radioactive marker is distinguishable from the gamma radiation emitted from the lesion, wherein the radioactive marker is contained within a fixed-geometry tube having a proximal tube portion extending in a first direction and a distal tube portion extending in a second, different direction, with the proximal tube portion and the distal tube portion charged with the radioactive marker such that the tube contains the radioactive marker along the tube in both the first direction and in the second, different direction such that the effect of radioactive marker extending in both the first and second directions is usable to determine the position and orientation of the hollow tube using the positron emission tomography device;
    causing the tube to be sealed at a proximal end of said proximal tube portion and at a distal end of said distal tube portion;
    introducing the tube into the body part;
    anchoring the tube proximal portion to the lesion; and
    detecting the position and orientation of the tube by detecting the radioactive marker in both the proximal tube portion and the distal tube portion.

2. The method of claim 1, wherein the radioactive marker includes a source of radioisotope, the radioisotope being selected from the group consisting of 2[F-18]fluorodeoxyglucose, sodium-22, cobalt-57, and germanium-68.

3. The method of claim 1, wherein the step of using the detected gamma radiation to determine the positional data comprises:
    using at least two detector heads to detect gamma rays;
    using a coincident timing window to determine lines of response; and
    using the lines of response to form a representation of a distribution of positron-emitting sources in the body part.

4. A method for using positron nuclear emission image guidance to obtain positional data relating to a lesion in a body part into which a radiopharmaceutical substance has been injected, the method comprising the steps of:
    detecting gamma radiation emitted from the lesion in the body part using a positron emission tomography device;
    using the detected gamma radiation to determine the positional data; data;
    inserting a fixed-geometry radioactive marker into the body part, wherein gamma radiation emitted from the radioactive marker is distinguishable from the gamma radiation emitted from the lesion, wherein the radioactive marker is contained within a fixed-geometry tube having a proximal tube portion extending in a first direction and a distal tube portion extending in a second, different direction, with the proximal tube portion and the distal tube portion charged with the radioactive marker such that the tube contains the radioactive marker along the tube in both the first direction and in the second, different direction such that the effect of radioactive marker extending in both the first and second directions is usable to determine the position and orientation of the hollow tube using the positron emission tomography device;
    sealing the tube at a proximal end of said proximal tube portion and at a distal end of said distal tube portion;
    introducing the tube into the body part;
    anchoring the tube proximal portion to the lesion; and
    detecting the position and orientation of the tube by detecting the radioactive marker in both the proximal tube portion and the distal tube portion.

5. The method of claim 4, wherein the radiopharmaceutical substance is selected from the group consisting of FDG and sestamibi.

6. The method of claim 4, wherein the radioactive marker includes a source of radioisotope, the radioisotope being selected from the group consisting of sodium-22, germanium-68, 2[F-18]fluorodeoxyglucose, and cobalt-57.

7. The method of claim 4, wherein the step of using the detected gamma radiation to determine the positional data comprises:
    using at least two detector heads to detect gamma rays;
    using a coincident timing window to determine lines of response; and
    using the lines of response to form a representation of a distribution of nuclei-emitting sources in the body part.

8. An interventional procedure kit that can be used in conjunction with a positron emission tomography (PET) scanner system for obtaining image data relating to a compressed and/or immobilized body part, the system comprising a first detector head and a second detector head, wherein each of the first and second detector heads includes materials that are sensitive to gamma radiation emitted from the body part; and wherein coincidence gating is applied between signals detected by the first and second detector heads; and
    wherein a result of the applied coincidence gating is used to determine the image data, the interventional procedure kit comprising:

a fixed-geometry wire having a proximal portion extending in a first direction and a distal portion extending in a second, different direction, both the proximal portion and the distal portion being filled with radioactive material such that both the direction and orientation of the positron wire are detectable with the positron emission tomography scanner system, the gamma radiation from the fixed-geometry wire being distinguishable from the gamma radiation emitted by the body part, the wire being sealed at a distal section and at a proximal section to seal the radioactive material within the proximal portion and the distal portion.

9. The interventional procedure kit of claim 8, wherein the wire includes an anchoring bend, disposed between the proximal portion and the distal portion, for anchoring the wire in a position within the body part.

10. The interventional procedure kit of claim 8, wherein the wire includes an anchoring barb for anchoring the wire in a position within the body part.

11. The interventional procedure kit of claim 8, wherein the radioactive material includes a radiopharmaceutical selected from the group consisting of FDG and sestamibi.

12. The interventional procedure kit of claim 8, wherein the radioactive material includes a source of radioisotope, the radioisotope being selected from the group consisting of sodium-22, germanium-68, 2[F-18]fluorodeoxyglucose, and cobalt-57.

13. A method of marking a lesion in a body part, comprising the steps of:
obtaining a first positron-emission image of the body part from gamma radiation emitted therefrom;
determining an approximate position of the lesion from the first image;
percutaneously introducing a cannula to the determined approximate position;
inserting a fixed geometry wire into the cannula, the wire having a proximal portion extending in a first direction and a distal portion extending in a second, different direction, both the proximal portion and the distal portion being filled with a radioactive material such that both the direction and orientation of the wire are detectable with positron emission tomography, the wire being sealed at a distal section and at a proximal section to seal the radioactive material within the proximal portion and the distal portion, the gamma radiation from the fixed-geometry wire being distinguishable from the gamma radiation emitted by the body part;
retracting the cannula while holding the wire in place; and
obtaining a second positron-emission image of the body part, wherein the second image includes data relating to a position of the lesion and data relating to the position and orientation of the wire.

14. The method of claim 13, wherein the radioactive material includes a radiopharmaceutical selected from the group consisting of FDG and sestamibi.

15. The method of claim 13, wherein the radioactive material includes a source of radioisotope, the radioisotope being selected from the group consisting of sodium-22, germanium-68, and cobalt-57.

16. A method for using positron emission image guidance to enable an intervention relating to a lesion in a portion of tissue within a body part, the method comprising the steps of:
obtaining a first positron emission tomograph of the portion of tissue from gamma radiation emitted therefrom;
determining spatial coordinates of the portion of tissue;
using the determined spatial coordinates to determine a desired position and orientation for a radioactive marker;
introducing a fixed-geometry tube containing the radioactive marker into the portion of tissue, the tube having a proximal tube portion extending in a first direction and a distal tube portion extending in a second, different direction, with the proximal tube portion and the distal tube portion charged with the radioactive marker such that the tube contains the radioactive marker along the tube in both the first direction and in the second, different direction such that the radioactive marker is usable to determine the position and orientation of the tube using a positron emission tomography device, the gamma radiation from the fixed-geometry tube being distinguishable m the gamma radiation emitted by the portion of the tissue;
obtaining a second positron emission tomograph of the portion of tissue, the second tomograph including data relating to the position and orientation of the radioactive marker; and
positioning an interventional device using the second tomograph.

17. The method of claim 16, further comprising the steps of:
using the second tomograph to determine whether the radioactive marker is correctly positioned and oriented in the second tomograph; and
when it is determined that the radioactive marker is not correctly positioned and oriented, adjusting a position or orientation of the radioactive marker and obtaining an additional positron emission tomograph of the portion of tissue that includes data relating to the adjusted position and orientation of the radioactive marker.

18. The method of claim 16, further comprising the step of removing the radioactive marker.

19. The method of claim 16, further comprising the step of affixing the radioactive marker to the interventional device.

20. The method of claim 19, further comprising the steps of:
commencing performance of an intervention; and
obtaining an additional positron emission tomograph during the intervention.

21. The method of claim 19, further comprising the steps of:
commencing performance of an intervention;
completing the intervention; and
obtaining an additional positron emission tomograph after the intervention.

22. The method of claim 16, further comprising the step of placing the radioactive marker within the interventional device.

23. The method of claim 22, further comprising the steps of:
commencing performance of an intervention; and
obtaining an additional positron emission tomograph during the intervention.

24. The method of claim 22, further comprising the steps of:
commencing performance of an intervention;
completing the intervention; and
obtaining an additional positron nuclear emission tomograph after the intervention.

25. A positron emission tomography system for obtaining image data relating to a compressed and/or immobilized body part, the system comprising:

a fixed-geometry wire that is charged with a radioactive marker, the wire having a proximal portion extending in a first direction and a distal portion extending in a second, different direction, both the proximal portion and the distal portion being filled with the radioactive marker such that both the direction and orientation of the wire are detectable with positron emission tomography, the wire being sealed at a distal section and at a proximal section to seal the radioactive material within the proximal portion and the distal portion;

an apparatus for detecting gamma radiation emitted by a lesion in a body part; and an apparatus for detecting positron emission data, wherein when the wire is positioned near a the lesion in the body part, the system is configured to provide image data for enabling an interventional device to be positioned and oriented for performance of an intervention relating to the lesion, the gamma radiation from the fixed-geometry wire being distinguishable from gamma radiation emitted by the lesion.

* * * * *